US012653921B2

(12) United States Patent
Sordo et al.

(10) Patent No.: US 12,653,921 B2
(45) Date of Patent: Jun. 16, 2026

(54) DEVICE FOR DIFFUSING VOLATILE SUBSTANCES

(71) Applicant: Zobele Holding SPA, Trento (IT)

(72) Inventors: Walter Sordo, Trento (IT); Stefano Deflorian, Trento (IT)

(73) Assignee: Zobele Holding, S.p.A, Trento (IT)

( * ) Notice: Subject to any disclaimer, the term of this patent is extended or adjusted under 35 U.S.C. 154(b) by 510 days.

(21) Appl. No.: 18/038,049

(22) PCT Filed: Nov. 17, 2021

(86) PCT No.: PCT/EP2021/081950
§ 371 (c)(1),
(2) Date: May 22, 2023

(87) PCT Pub. No.: WO2022/106450
PCT Pub. Date: May 27, 2022

(65) Prior Publication Data
US 2023/0355824 A1 Nov. 9, 2023

(30) Foreign Application Priority Data

Nov. 20, 2020 (EP) .................................... 20208868

(51) Int. Cl.
*A61L 9/12* (2006.01)
(52) U.S. Cl.
CPC .................................... *A61L 9/127* (2013.01)
(58) Field of Classification Search
CPC .................................................... A61L 9/127
See application file for complete search history.

(56) References Cited

U.S. PATENT DOCUMENTS 3,727,840 A 4/1973 Nigro

FOREIGN PATENT DOCUMENTS

| BE | 1007062 | 3/1995 |
|---|---|---|
| DE | 102014017960 | 6/2016 |
| EP | 1640039 | 3/2006 |
| EP | 2357011 | 8/2011 |
| GB | 738173 | 10/1955 |
| WO | WO 2006/061803 | 6/2006 |

OTHER PUBLICATIONS

International Search Report and the Written Opinion Dated Feb. 16, 2022 From the International Searching Authority Re. Application No. PCT/EP2021/081950. (10 Pages).

*Primary Examiner* — Timothy C Cleveland

(57) ABSTRACT

Device for diffusing volatile substances that comprises a container (1), an upper closing element (2) which closes the opening of the container (1) and a wick (3) jointed to the closing element (2). The container (1) comprises an opening, a reservoir containing a predetermined volume of a liquid volatile substance, and a lower neck (6). The closing element (2) further comprises at least one internal perimetral grove (4), and the lower neck (6) of the container (1) further comprises a groove with no thread pitch (7) in turn comprising protrusions (9) so that the internal perimetral grove (4) and the groove with no thread pitch (7) work together for an adjustment on a fixed pre-determined position of the upper closing element (2) with regards to the container (1).

5 Claims, 4 Drawing Sheets

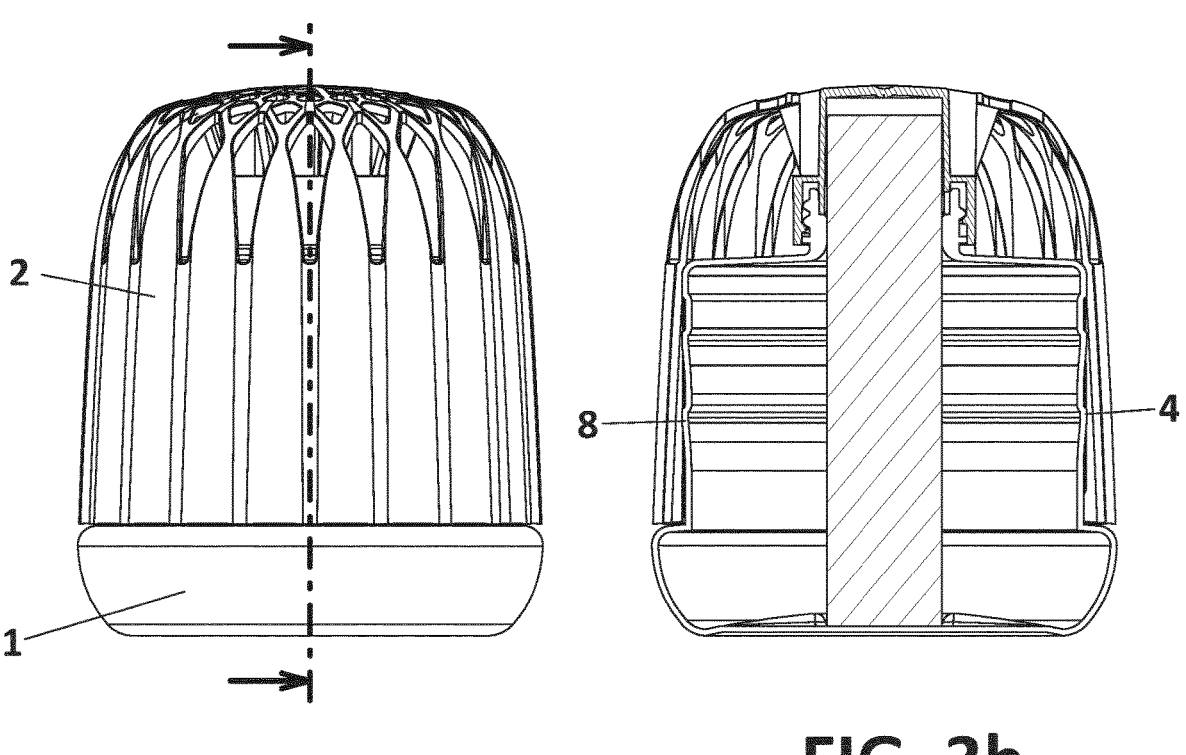
FIG. 3a
FIG. 3b
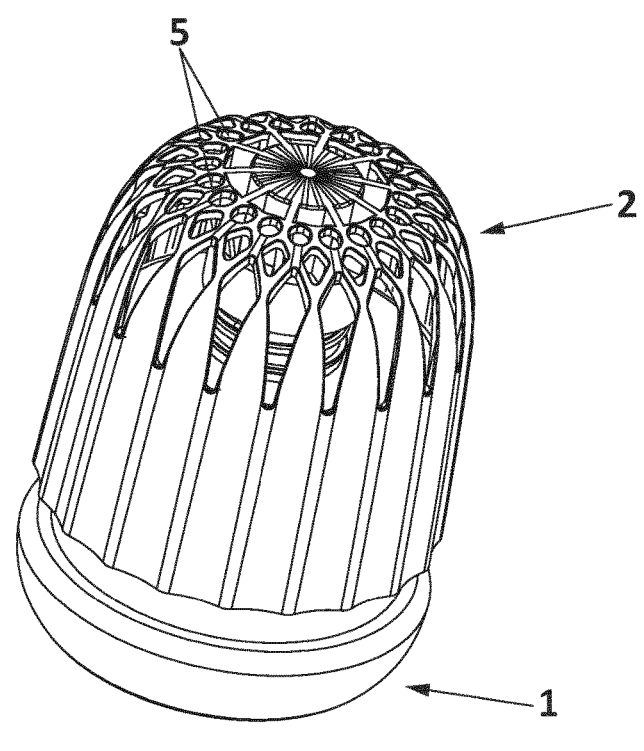
FIG. 3c

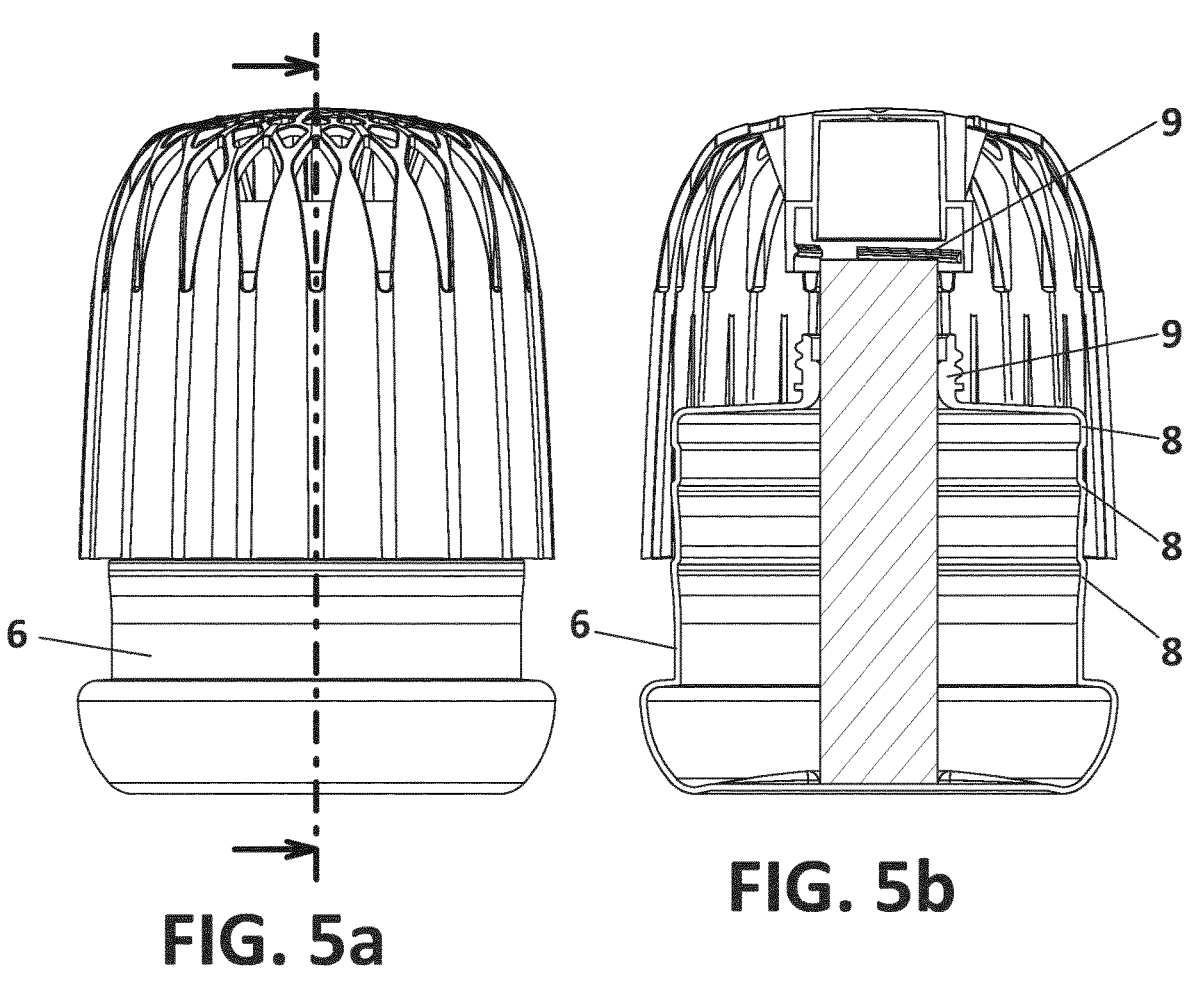
FIG. 5a
FIG. 5b
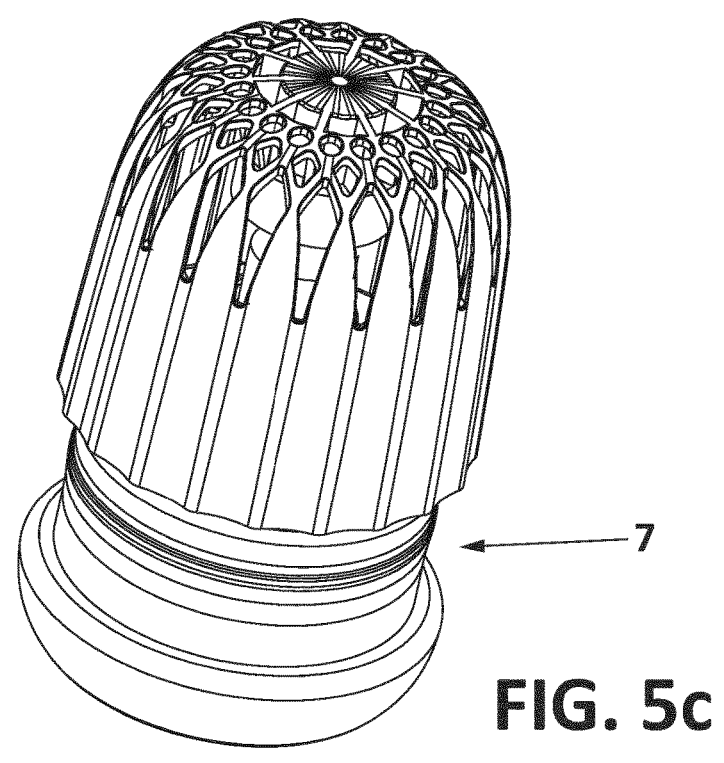
FIG. 5c

DEVICE FOR DIFFUSING VOLATILE SUBSTANCES

RELATED APPLICATIONS

This application is a National Phase of PCT Patent Application No. PCT/EP2021/081950 having International filing date of Nov. 17, 2021, which claims the benefit of priority of Europe patent application No. 20208868.8 filed on Nov. 20, 2020. The contents of the above applications are all incorporated by reference as if fully set forth herein in their entirety.

FIELD AND BACKGROUND OF THE INVENTION

The present invention falls within the technical field of devices for the disinfection, sterilization or deodorization of air and concerns in particular a device for the diffusion of volatile substances.

The device comprises a diffusing wick, a container for the volatile substance and an upper closing element which serves as a lid, ornament and regulator and to which the wick is attached. The container and the upper element are connected to each other by a thread located in the neck of the container and which serves only to close or open the bottle, while adjustment is made by sliding the upper element, using the side walls of the bottle as a guide. It also comprises a perimeter groove with no thread pitch which serves to define predefined evaporation positions for the wick.

Various types of devices for the diffusion of volatile substances such as air fresheners or insecticides are known on the market. Among them, it is worth mentioning those that need a connection with an electricity outlet for their operation and those that do not require the use of electricity.

The former include an interior fan that helps to diffuse the aroma of the volatile substance, while the latter generally consist of a container that contains the volatile substance and allows the exit of a wick that is partially in contact with the substance, from which the aroma is diffused outwards.

In the current state of the art there are several patent documents concerning non-electrical devices for the diffusion of volatile substances. For example, the European patent with publication number EP2357011 discloses a dispenser for volatile liquids which consists of a bottle in which is the liquid to be diffused, a liquid in which a wick is partially bathed; a shutter cover mounted on said snap-on bottle while having the possibility of turning around its axis without translation, said cover being provided with slots or windows for the passage of air; a wick support snapped onto the neck of said bottle and blocked in rotation, this support being in the form of a sleeve provided with slots or windows for the passage of air and an external thread; and a plug comprising, on the one hand, an internally threaded skirt to be engaged with the external thread of said wick support and further comprising external vertical grooves intended to engage with the vertical sleeve integral with the upper part of said cover and, on the other hand, an inner sleeve forming a sealing cap for said wick.

This dispenser has some drawbacks. Among them it has to be mentioned that the movements of opening regulation and closure movement of the bottle are incompatible with each other. Regulation movement requires a speed and range of movement in the direction parallel to the axis of the wick that is incompatible with applying a torque sufficient to close the bottle robustly.

In addition, the existence of a thread on the outside of the bottle, which is coupled with the upper cover, prevents air from entering there. The internal space around the wick is therefore only open at the top, which prevents a generous flow of air and therefore limits evaporation.

European patent number EP1640039 discloses an adjustable, non-electric liquid air-freshener device that comprises a vessel containing scented liquid, a wick partially submerged in the liquid, a stopper coupled on the mouth of the vessel and a cap that covers the stopper. It also has a lower tubular portion provided with two windows and an inner threaded segment that unscrews from a central threaded tubular portion of the stopper as the cap is turned, raising it and gradually revealing the windows so that the wick is exposed to the exterior, facilitating the adjustable evaporation of the scented liquid. The cap is provided with flexible stops that are prolonged externally from the base of its lower tubular portion and as they rise meet a trapezoidal inner peripheral flange defined in a cylindrical body of the stopper to prevent the exit of the cap.

U.S. Pat. No. 3,727,840 discloses a container for dispersant material comprising first and second members adapted to be movably connected together, the first member having wick means disposed therein in communication with a surrounding atmosphere, the second member having therein a sealed reservoir containing fluid dispersant material. The first member further includes means for opening the reservoir, whereby upon relative movement of the first and second members toward each other the reservoir opening means operates to open the reservoir, permitting flow of the dispersant material therefrom onto the wick means.

None of these patents disclose a device for the diffusion of volatile substances built in a simple and robust manner on which, for instance, the bottle and the upper element are connected to each other through a thread located in the bottle neck which only serves to close or open the bottle, while the adjustment of the wick is made simply by sliding the upper element using the side walls of the bottle as a guide.

It is also desirable that such an easy body comprises regulation means to fix the exposure of the wick, and therefore the amount of evaporation. Therefore, the above-mentioned drawbacks of the current state of the art are easily overcome.

SUMMARY OF THE INVENTION

The object of the invention is a device for diffusing volatile substances built in a simple and robust manner which comprises a container able to contain a volume of a liquid volatile substance, an upper closing element which serves as a lid for the container, and a wick jointed to the closing element, which is soaked with the liquid volatile substance and diffuses its scent or any other features to the air space surrounding the device.

The possibility of exposing different lengths of the wick by means of the cap expands the field of use of such evaporators, which can now also dispense a predetermined amount of liquid in vapor form.

The container and the closing element are preferably produced as injection molded parts. They comprise elements that work together to enable a lateral movement between the container and the closing element. A slight lift of the cap relative to the container releases a small gap in the wick to allow small amounts of liquid to evaporate. A stronger lateral movement between the container and the cap leads to less covering of the wick and thus to a larger evaporator gap, which enables a stronger evaporation per unit of time.

On the preferred embodiment, the closing element comprises an internal perimetral groove located near a lower end, and the container has a neck on which a groove with no thread pitch is defined. Therefore, the container and the closing element are connected to each other by respectively the groove with no thread pitch and the internal perimetral groove, which work together for an adjustment of the position between both elements.

It is envisaged in a preferred embodiment of the device that the closing element has holes through which the wick can emit vapours to the environment. They also have the advantage that it can be seen how much wick is covered and whether the wick is still soaked in liquid.

BRIEF DESCRIPTION OF THE SEVERAL VIEWS OF THE DRAWINGS

As a complement to the description provided herein, and for the purpose of helping to make the features of the invention more readily understandable, in accordance with a preferred practical exemplary embodiment thereof, said description is accompanied by a set of drawings which, by way of illustration and not limitation, represent the following:

FIG. 3a.—Shows a front view of the device on a first position of the regulation of the evaporation.

FIG. 3b.—Shows a sectioned front view of the device on the first position.

FIG. 3c.—Shows a top perspective view of the device on the first position.

FIG. 5a.—Shows a front view of the device on a third position of the regulation of the evaporation.

FIG. 5b.—Shows a sectioned front view of the device on the third position.

FIG. 5c.—Shows a top perspective view of the device on the third position.

DESCRIPTION OF SPECIFIC EMBODIMENTS OF THE INVENTION

A detailed explanation of a preferred embodiment of the object of the present invention is provided below with the aid of the aforementioned figures.

Figure 1:
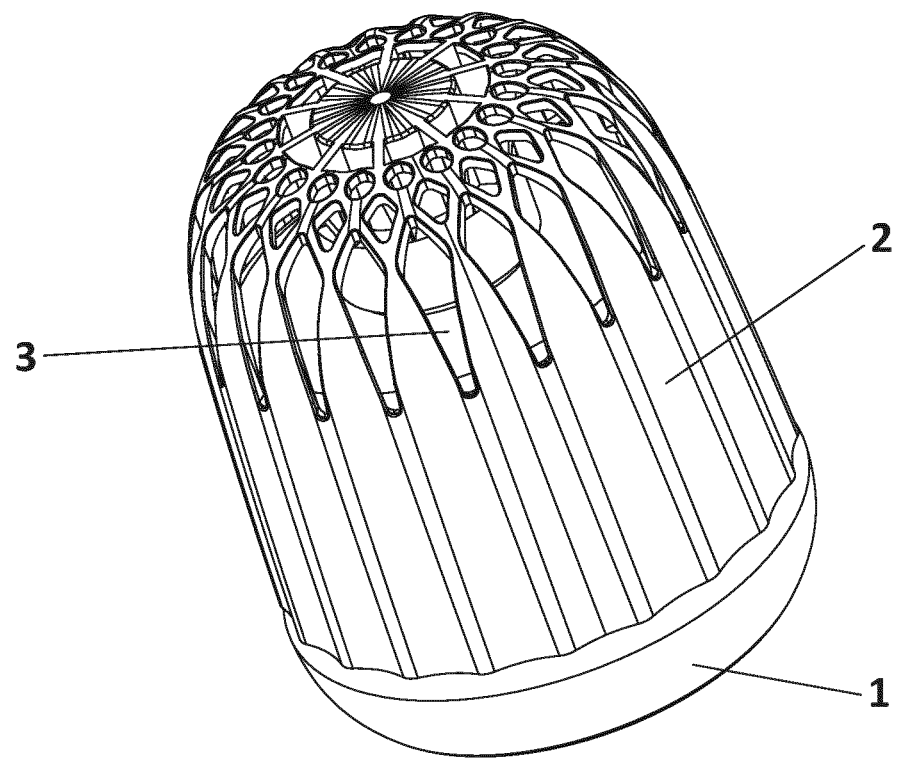
FIG. 1.—Shows a top perspective view of the device for the diffusion of volatile substances on a closed position.
Figure 2:
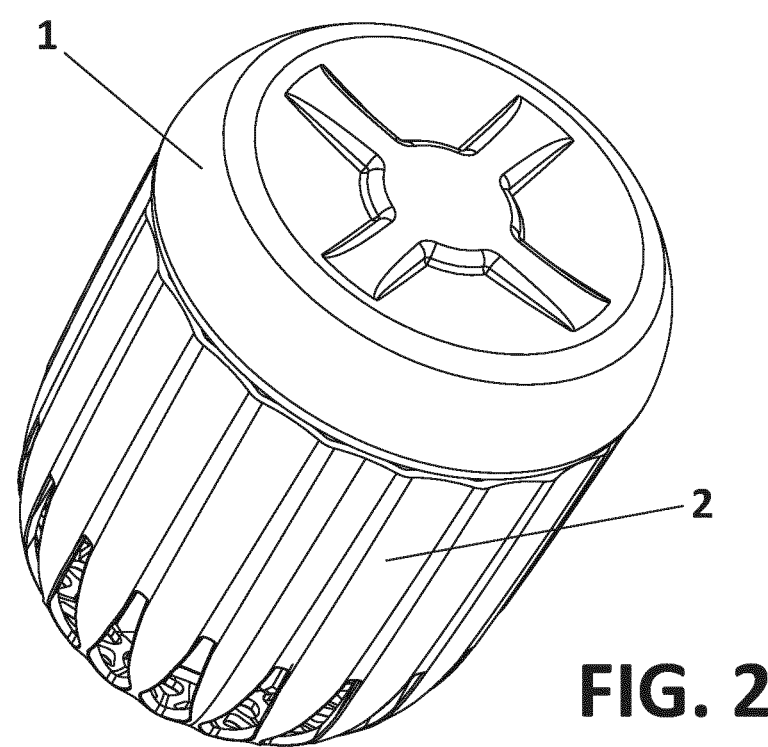
FIG. 2.—Shows a bottom perspective view of the device.

The device for diffusing volatile substances, shown in FIGS. 1-2, essentially comprises a container (1), an upper closing element (2) which serves as a lid for the container (1) and a wick (3) jointed to the closing element (2), which in turn comprises an upper end and a lower end. Inside the container (1) there is a reservoir intended to contain a predetermined volume of a liquid volatile substance and connected with the outside through an opening. The lower end of the wick (3) protrudes into the liquid, while the upper end protrudes from the liquid and from the container (1).

A lower section of the wick (3) extends over the length into the liquid of the reservoir, an upper section of the wick (3) protrudes from the container (1) and an intermediate section of the wick (3) lies in an area inside the container (1) but outside the liquid.

The closing element (2) comprises at least one internal perimetral groove (4), which in this preferred embodiment is located near a lower end. The closing element (2) also has an outer diameter which corresponds to the outer diameter of the container (1). At the upper end of the closing element (2) there are through holes (5), as well as external ribs conceived to ease the handling of the device.

The container (1) has in turn a lower neck (6) on which a groove with no thread pitch (7) is defined. Therefore, the container (1) and the closing element (2) are movably connected to each other by respectively the groove with no thread pitch (7) and the internal perimetral groove (4), which work together for an adjustment of the relative position between both elements. In turn, the closing element (2) slides upwards and downwards across the container (1) using the lower neck (6) of the container (1) as a guide.

Figures 4A, 4B, 4C:
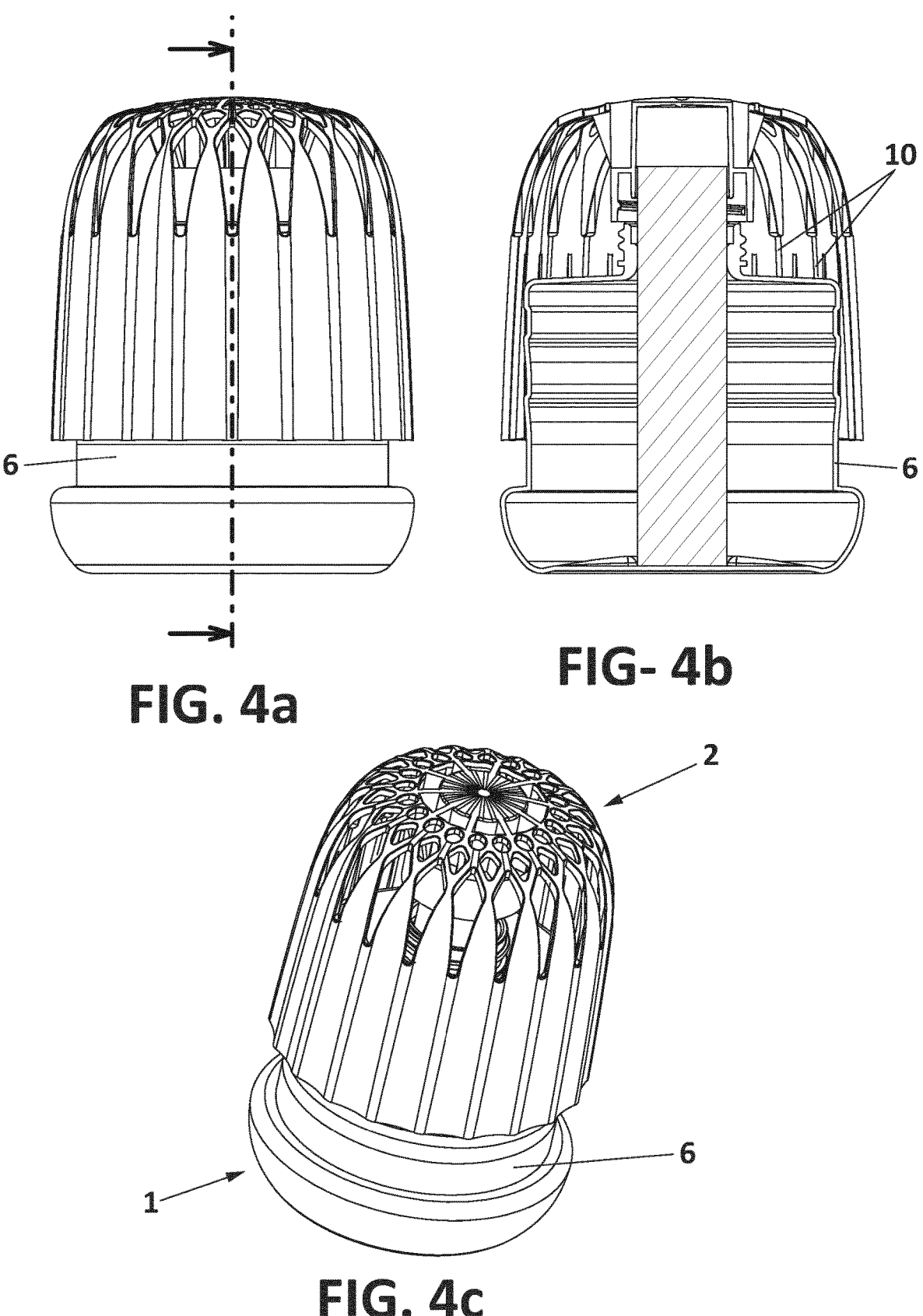
FIG. 4a.—Shows a front view of the device on a second position of the regulation of the evaporation.
FIG. 4b.—Shows a sectioned front view of the device on the second position.
FIG. 4c.—Shows a top perspective view of the device on the second position.

At it can be seen in FIGS. 3b, 4b and 5b, in this preferred embodiment the groove with no thread pitch (7) comprises three protrusions (8) that define three correspondent positions for the closing element (2): a first lower position, a second intermediate position and a third upper position. On each of them the internal perimetral groove (4) is blocked by one of the positions of the groove with no thread pitch (7), thereby defining three different exposure degrees of the wick (3).

On the closed position of the device shown on FIGS. 1 and 2 the container (1) and the closing element (2) are mutually joint to each other by means of a correspondent internal mutual closing thread (9) which prevents an undesired opening of the device with the subsequent diffusion of the vapours during the storage, transport and/or exhibition of said device.

On the preferred embodiment described here, the closing element (2) further comprises vertical internal ribs (10) that reinforce its resistance. In this case, the internal perimetral groove (4) is made over a lower end of each rib (10), therefore being discontinuous.

Starting from the closed position shown on FIGS. 1 and 2, when a user wants the device to emit the volatile substance contained therein has firstly to unscrew the closing element (2) from the container (1), therefore operating on the closing thread (9).

Once separated from the container (1), the closing element (2) slides upwards relative to the container (1), manually operated by the user, and the closing element (2) lifts off relative to the container (1) until the internal perimetral groove (4) is intercepted by the lower protrusion (8), as seen in FIGS. 3a-3c. In this position, vapours from the wick soaked with the liquid volatile substance pass through the through holes (5) to the air space surrounding the device.

On a situation in which further evaporation is needed, the user manually turns and pulls up the closing element (2) up to a second position, as shown in FIG. 4a-4c, or even up to a third position, as shown in FIGS. 5a-5c. On each of these positions, the internal perimetral groove (4) is intercepted by respectively the intermediate protrusion (8) and the upper protrusion (8).

The invention claimed is:

1. A device for diffusing volatile substances that comprises:

a container which comprises:

an opening;

a reservoir containing a predetermined volume of a liquid volatile substance; and a lower neck;

an upper closing element which closes the opening of the container and slides upwards and downwards across the neck; and a wick which comprises an upper end and a lower end, wherein the lower protrudes into the liquid, while the upper end protrudes from the liquid and from the container;

being the device characterized in that:

the closing element further comprises at least one internal perimetral groove, and the lower neck of the container further comprises a groove with no thread pitch, the groove with no thread pitch comprising a plurality of protrusions;

wherein the internal perimetral groove and the plurality of protrusions work together for an adjustment on a fixed pre-determined position of the upper closing element with regards to the container.

2. The device for diffusing volatile substances according to claim 1 wherein the container and the closing element are mutually joint to each other by means of a correspondent closing thread.

3. The device for diffusing volatile substances according to claim 1 wherein the closing element further comprises vertical internal ribs for structural reinforcement.

4. The device for diffusing volatile substances according to claim 3 wherein the internal perimetral groove is made over the lower end of each rib, therefore being discontinuous.

5. The device for diffusing volatile substances according to claim 1 wherein the closing element further comprises through holes.

*     *     *     *     *